(12) United States Patent
Wang et al.

(10) Patent No.: US 12,385,897 B1
(45) Date of Patent: Aug. 12, 2025

(54) REAL-TIME QUANTITATIVE CHARACTERIZATION METHOD, EQUIPMENT AND MEDIUM FOR ROCK MASS EVOLUTION

(71) Applicant: Institute of Geology and Geophysics,CAS, Beijing (CN)

(72) Inventors: Zan Wang, Beijing (CN); Shengwen Qi, Beijing (CN); Bowen Zheng, Beijing (CN); Wang Zhang, Beijing (CN); Bo Wan, Beijing (CN); Xiaokun Hou, Beijing (CN); Wei Lu, Beijing (CN); Guangming Luo, Beijing (CN); Lina Ma, Beijing (CN); Yongchao Li, Beijing (CN); Guoliang Li, Beijing (CN); Yuran Zhang, Beijing (CN); Weiwei Zhu, Beijing (CN); Wenjie Hao, Beijing (CN); Songfeng Guo, Beijing (CN); Yu Zou, Beijing (CN); Jianing Cong, Beijing (CN); Chao Jin, Beijing (CN); Tianming Huang, Beijing (CN); Yanlong Kong, Beijing (CN)

(73) Assignee: Institute of Geology and Geophysics, CAS, Beijing (CN)

(*) Notice: Subject to any disclaimer, the term of this patent is extended or adjusted under 35 U.S.C. 154(b) by 0 days.

(21) Appl. No.: 19/093,196

(22) Filed: Mar. 27, 2025

(30) Foreign Application Priority Data

Nov. 15, 2024 (CN) .......................... 202411629410.2

(51) Int. Cl.
*G01N 33/24* (2006.01)
*G06N 3/045* (2023.01)

(52) U.S. Cl.
CPC ............. *G01N 33/24* (2013.01); *G06N 3/045* (2023.01)

(58) Field of Classification Search
CPC ........... G01N 33/24; G01N 2203/0218; G01N 2203/0284; G01N 24/081; G01N 3/08;
(Continued)

(56) References Cited

U.S. PATENT DOCUMENTS 10,400,590 B1 * 9/2019 Aldred .................... E21B 49/00
11,341,410 B1 5/2022 Johnson et al.
(Continued)

FOREIGN PATENT DOCUMENTS

| CN | 113777278 A | 12/2021 |
| CN | 114965234 A | 8/2022 |

*Primary Examiner* — Michael S Osinski
(74) *Attorney, Agent, or Firm* — Nitin Kaushik

(57) ABSTRACT

A real-time quantitative characterization method, equipment and a medium for rock mass evolution are disclosed. The method includes: the multiphase field detection and monitoring data is fused; a deep learning model driven by physical principles is established based on the physical principles of fluid density; the deep learning model is trained using real-time fused data as input and corresponding evolution distribution images as output; a trained deep learning model is used to obtain an evolution distribution image based on multi-phase field detection and monitoring data of different time periods and types; a mathematical model is used to quantitatively characterize of physical and mechanical parameters in the whole process of progressive failure of the dynamic evolution of the rock mass based on the macroscopic mechanical parameters and evolution distribution images synchronized with multiphase field detection and monitoring data.

9 Claims, 4 Drawing Sheets

(58) Field of Classification Search
CPC .......... G06N 3/045; G06N 3/08; G06N 3/082; G01V 1/282; G01V 1/301; G01V 1/306; G01V 2210/62; E21B 2200/22; E21B 25/00; E21B 49/02
See application file for complete search history.

(56) References Cited

U.S. PATENT DOCUMENTS

| | | | |
|---|---|---|---|
| 11,585,802 B1* | 2/2023 | Qi | G01N 33/24 |
| 11,615,519 B2* | 3/2023 | Shen | G06T 7/0004 |
| | | | 382/103 |
| 11,789,172 B2* | 10/2023 | Kazama | G01V 1/01 |
| | | | 702/14 |
| 11,989,655 B2* | 5/2024 | Luo | G10L 25/03 |
| 12,331,988 B2* | 6/2025 | Yang | F25D 29/00 |
| 2017/0131192 A1* | 5/2017 | Perez | G01N 3/08 |
| 2018/0052249 A1* | 2/2018 | Chen | G01V 20/00 |
| 2019/0353813 A1* | 11/2019 | Cobos | G06F 30/20 |
| 2021/0223424 A1* | 7/2021 | Valensi | G01V 1/303 |
| 2023/0084240 A1* | 3/2023 | Zhang | G01V 20/00 |
| | | | 382/157 |
| 2023/0408431 A1* | 12/2023 | De Kort | G01N 24/081 |
| 2024/0230495 A1* | 7/2024 | Feng | G01N 3/08 |
| 2024/0319396 A1* | 9/2024 | Sun | G01V 1/50 |
| 2024/0352845 A1* | 10/2024 | Noufal | E21B 47/002 |
| 2024/0418890 A1* | 12/2024 | Rickett | G01V 1/3843 |
| 2025/0061701 A1* | 2/2025 | Zhao | G06V 10/806 |
| 2025/0067644 A1* | 2/2025 | Liu | G01N 3/08 |
| 2025/0110249 A1* | 4/2025 | Liu | G01V 1/305 |
| 2025/0155596 A1* | 5/2025 | Feng | G01V 1/30 |

* cited by examiner

ND EAL-TIME QUANTITATIVE
CHARACTERIZATION METHOD,
EQUIPMENT AND MEDIUM FOR ROCK
MASS EVOLUTION

CROSS-REFERENCE TO RELATED APPLICATIONS

This patent application claims the benefit and priority of Chinese Patent Application No. 202411629410.2, entitled "REAL-TIME QUANTITATIVE CHARACTERIZATION METHOD, EQUIPMENT AND MEDIUM FOR ROCK MASS EVOLUTION" filed with the China National Intellectual Property Administration on Nov. 15, 2024, the disclosure of which is incorporated by reference herein in its entirety as part of the present application.

TECHNICAL FIELD

The present application relates to the testing field of reservoir rock mass engineering geomechanics test, in particular to a real-time quantitative characterization method, equipment and a medium for rock mass evolution.

BACKGROUND

The carbon dioxide geological storage project belongs to the deep geological engineering which is "inaccessible". The dynamic process and mechanism of fracture formation and evolution of deep rock mass under the action of multi-phase field coupling environment with multi-phase (supercritical, gas, liquid and solid) and multi-field (temperature, fluid, stress, chemistry and biology) has always been a "black box" problem.

The key to reveal the spatiotemporal response characteristics and the evolution laws of rock mass under the action of multiphase field coupling in the process of supercritical carbon dioxide injection disturbance is to realize the real-time transparency of multiphase field coupling rock mass evolution. Although the key information of rock mass structure evolution can be provided by the X-ray tomography, the nuclear magnetic resonance technology, the geophysical detection and the acoustic emission monitoring technology, there is a problem of structural imaging lag or poor imaging accuracy, which cannot realize the real-time and transparent characterization of multiphase field coupling rock mass evolution in carbon sequestration engineering. At present, the research on the high-precision imaging and the real-time transparent characterization of multiphase field coupling rock mass evolution is still in a blank state.

Therefore, based on the above problems, it is urgent to provide a real-time quantitative characterization method for the evolution of carbon sequestration engineering rock mass to open the black box of the dynamic evolution of rock mass under the disturbance of supercritical carbon dioxide injection.

SUMMARY

The purpose of present application is to provide a real-time quantitative characterization method, equipment, and a medium for rock mass evolution, which can achieve real-time transparent characterization of multiphase field long-time coupling rock mass evolution.

In order to achieve the above effects, the present application adopts the following technical solutions.

In the first aspect, the present application provides a real-time quantitative characterization method for rock mass evolution, which includes:
  acquiring both the evolution distribution images of the rock mass and real-time multiphase field detection and monitoring data at different evolution stages in the whole testing process of the multiphase field coupling test, wherein the evolution distribution images include a reconstructed pore distribution image, a pore fluid pressure distribution image and a supercritical carbon dioxide saturation distribution image; the multiphase field detection and monitoring data includes temperature, strain, resistivity, chemical ion concentration, microbial cell concentration, P wave velocity, S wave velocity and acoustic emission data;
  carrying out data fusion for the real-time multiphase field detection and monitoring data by using the feature extraction method and the Transformer deep learning model;
  establishing a deep learning model driven by physical principles by using the deep learning method according to the physical principles of fluid density under the influence of temperature, chemical ion concentration, microbial cell concentration and supercritical carbon dioxide;
  training the deep learning model driven by physical principles with the real-time fused data as input and the corresponding evolution distribution images as output;
  obtaining the evolution distribution images by adopting the trained deep learning model according to the multiphase field detection and monitoring data of different time and different types; and
  realizing the quantitative characterization of the physical and mechanical parameters in the whole process of the progressive failure of the dynamic evolution of the rock mass by adopting a mathematical model according to the macroscopic mechanical parameters and the evolution distribution images which are synchronous with the multiphase field detection and monitoring data; wherein the macroscopic mechanical parameters are the macroscopic mechanics parameters of different stages of rock mass evolution under the coupling action of different loading paths and multiphase fields.

Optionally, the device for acquiring the real-time multiphase field detection and monitoring data includes an optical fiber sensor, an electrode sensor, and an ultrasonic transducer.

Optionally, the deep learning method includes a Bayesian neural network, a convolutional neural network, a deep residual network, a recurrent neural network and a generative adversarial network.

Optionally, the mathematical model is established by logistic regression analysis, support vector machine (SVM), random forest or neural network.

In the second aspect, the present application provides a real-time quantitative characterization equipment for rock mass evolution, which includes:
  the data acquisition module, which is configured to acquire the evolution distribution images of the rock mass and real-time multiphase field detection and monitoring data at different evolution stages in the whole testing process of the multiphase field coupling test, wherein the evolution distribution images include a reconstructed pore distribution image, a pore fluid pressure distribution image and a supercritical carbon dioxide saturation distribution image; the multiphase field detection and monitoring data includes temperature, strain, resistivity, chemical ion concentration, microbial cell concentration, P wave velocity, S wave velocity and acoustic emission data;

the data fusion module, which is configured to carry out data fusion for the real-time multiphase field detection and monitoring data by using the feature extraction method and the Transformer deep learning model;

the deep learning model establishing module driven by physical principles, which is configured to establish a deep learning model driven by physical principles by using the deep learning method according to the physical principles of fluid density under the influence of temperature, chemical ion concentration, microbial cell concentration and supercritical carbon dioxide;

the deep learning model training module driven by physical principles, which is configured to train the deep learning model driven by physical principles with the real-time fused data as input and the corresponding evolution distribution images as output;

the evolution distribution images inversion module, which is configured to obtain the evolution distribution images by adopting the trained deep learning model according to the multiphase field detection and monitoring data of different time and different types; and the quantitative characterization module of physical and mechanical parameters, which is configured to realize the quantitative characterization of the physical and mechanical parameters in the whole process of the progressive failure of the dynamic evolution of the rock mass by adopting a mathematical model according to the macroscopic mechanical parameters and the evolution distribution images which are synchronous with the multiphase field detection and monitoring data.

In the third aspect, the present application provides a computer equipment, including: a memory, a processor, and a computer program stored on the memory and executable on the processor, wherein the processor executes the computer program to implement the real-time quantitative characterization method for rock mass evolution.

In the fourth aspect, the present application provides a computer-readable storage medium storing a computer program, the real-time quantitative characterization method for rock mass evolution will be implemented if the computer program executed by a processor.

According to the specific embodiments provided in present application, the following technical effects are disclosed.

The present application provides a real-time quantitative characterization method, equipment, and a medium for rock mass evolution. The deep learning model driven by physical principles is established by embedding controlling physical laws (i.e. partial differential equations) as prior information, combining differentiable programming methods with traditional numerical simulation methods (such as finite element method, finite difference method, or discrete element method), so that all numerical operations are implemented in differentiable building modules. The differentiable mechanism of the learning model driven by physical principles in this application solves forward and backward problems through automatic differentiation methods, and is relatively easy to combine with deep neural networks, thus having universality. This application utilizes feature extraction methods and Transformer deep learning models for data fusion of the real-time multiphase field detection and monitoring data, that is, multi-source heterogeneous massive information is fused and inverted to achieve efficient utilization of data and images of different formats, different magnitudes, different dimensions and different resolutions obtained by different detection and monitoring means; the key scientific problem of difficulty in training the deep learning model driven by physical principles is overcome to achieve the real-time transparent quantitative characterization of fine structural fields, effective stress fields, and supercritical carbon dioxide migration inside the multiphase field coupling rock mass.

BRIEF DESCRIPTION OF DRAWINGS

In order to more clearly illustrate the embodiments of the present application or technical solutions in the prior art, the accompanying drawings required for the embodiments will be described briefly. It is obvious that the drawings in the following description are only the embodiment of present application, and that those skilled in the art can obtain other drawings from these drawings without any creative efforts.

DETAILED DESCRIPTION OF THE EMBODIMENTS

In the following, the technical solutions in the embodiments of the present application will be clearly and completely described with reference to the drawings in the embodiments of the present application. Obviously, the described embodiments are only a part of the embodiments of the present application, but not all the embodiments thereof. Based on the embodiments of the present application, all other embodiments obtained by those skilled in the art without any creative efforts shall fall within the scope of the present disclosure.

In order to make the above objectives, features, and advantages of the present application more obvious and understandable, the following will provide further detailed explanations of the present application in conjunction with the accompanying drawings and specific embodiments.

Figure 1:
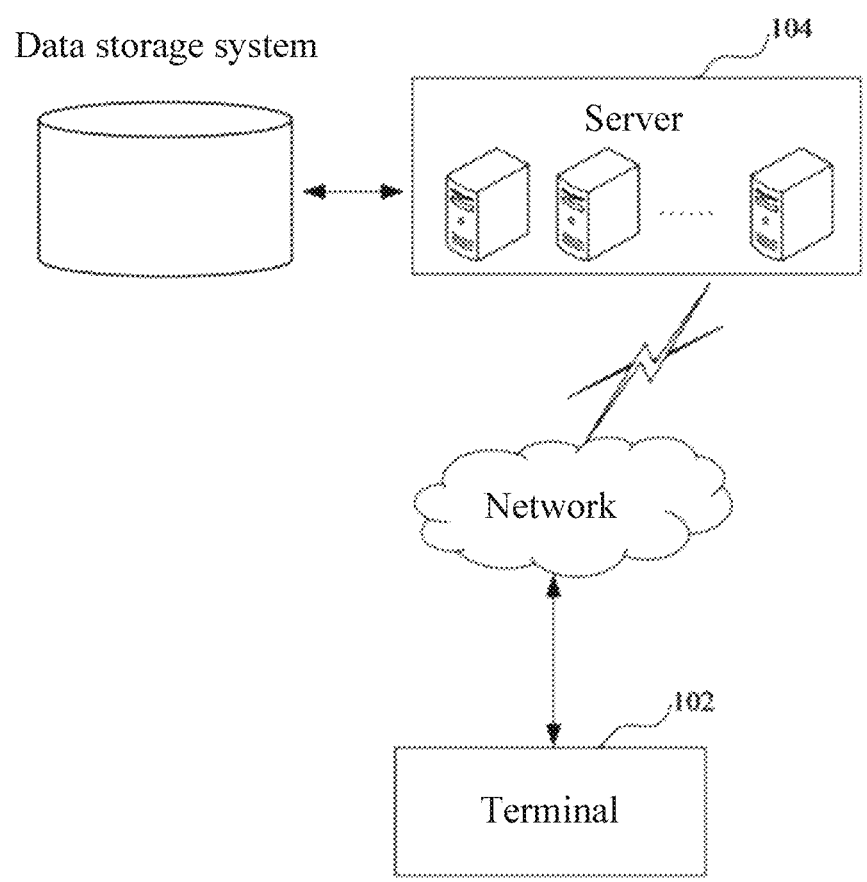
FIG. 1 is an application environment diagram of a real-time quantitative characterization method for rock mass evolution in an embodiment of the present application.

The real-time quantitative characterization method for rock mass evolution provided in the embodiments of this application can be applied to the application environment shown in the FIG. 1. Among them, the terminal 102 communicates with the server 104 through the network. The data storage system can store the data that the server 104 needs to process. The data storage system can be set up separately, integrated on the server 104, or placed on the cloud or other servers. The terminal 102 can send the multiphase field detection and monitoring data to be processed to the server 104. After receiving the multiphase field detection and monitoring data to be processed, the server 104 obtains the evolution distribution image based on the trained deep learning model. The quantitative characterization of the physical and mechanical parameters in the whole process of the progressive failure of the dynamic evolution of the rock mass is realized by adopting a mathematical model according to the macroscopic mechanical parameters and the evolution distribution images which are synchronous with the multiphase field detection and monitoring data; the server 104 can feed back the obtained quantitative characterization of the physical and mechanical parameters in the whole process of the progressive failure of the dynamic evolution of the rock mass to the terminal 102. In addition, in some embodiments, the real-time quantitative characterization method for rock mass evolution can also be implemented separately by the server 104 or the terminal 102. For example, the terminal 102 can directly process the multiphase field detection and monitoring data to be processed, or the server 104 can obtain the multiphase field detection and monitoring data to be processed from the data storage system and process it accordingly.

Figure 2:
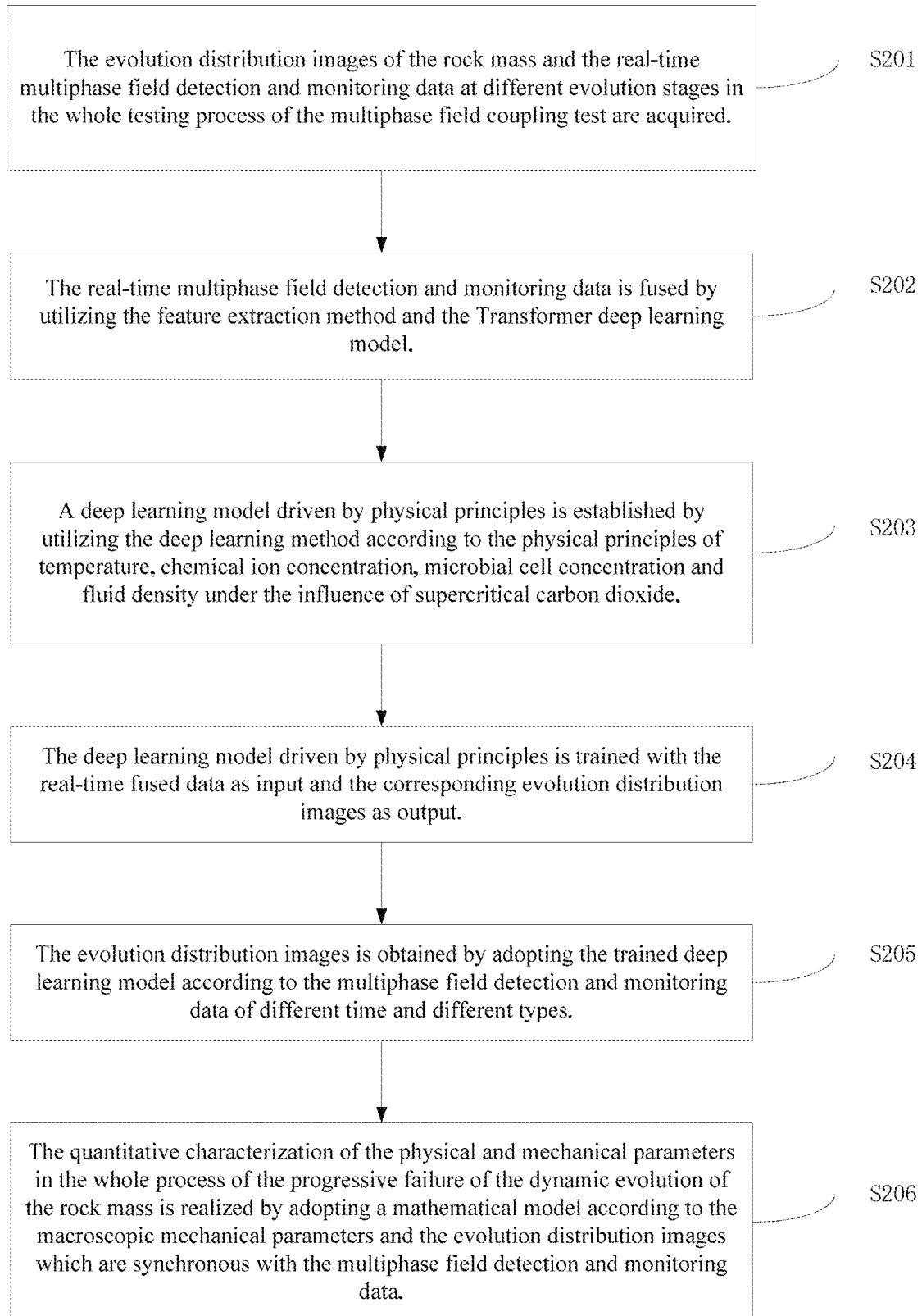
FIG. 2 is a flowchart of a real-time quantitative characterization method for rock mass evolution provided in an embodiment of the present application.
Figure 4:
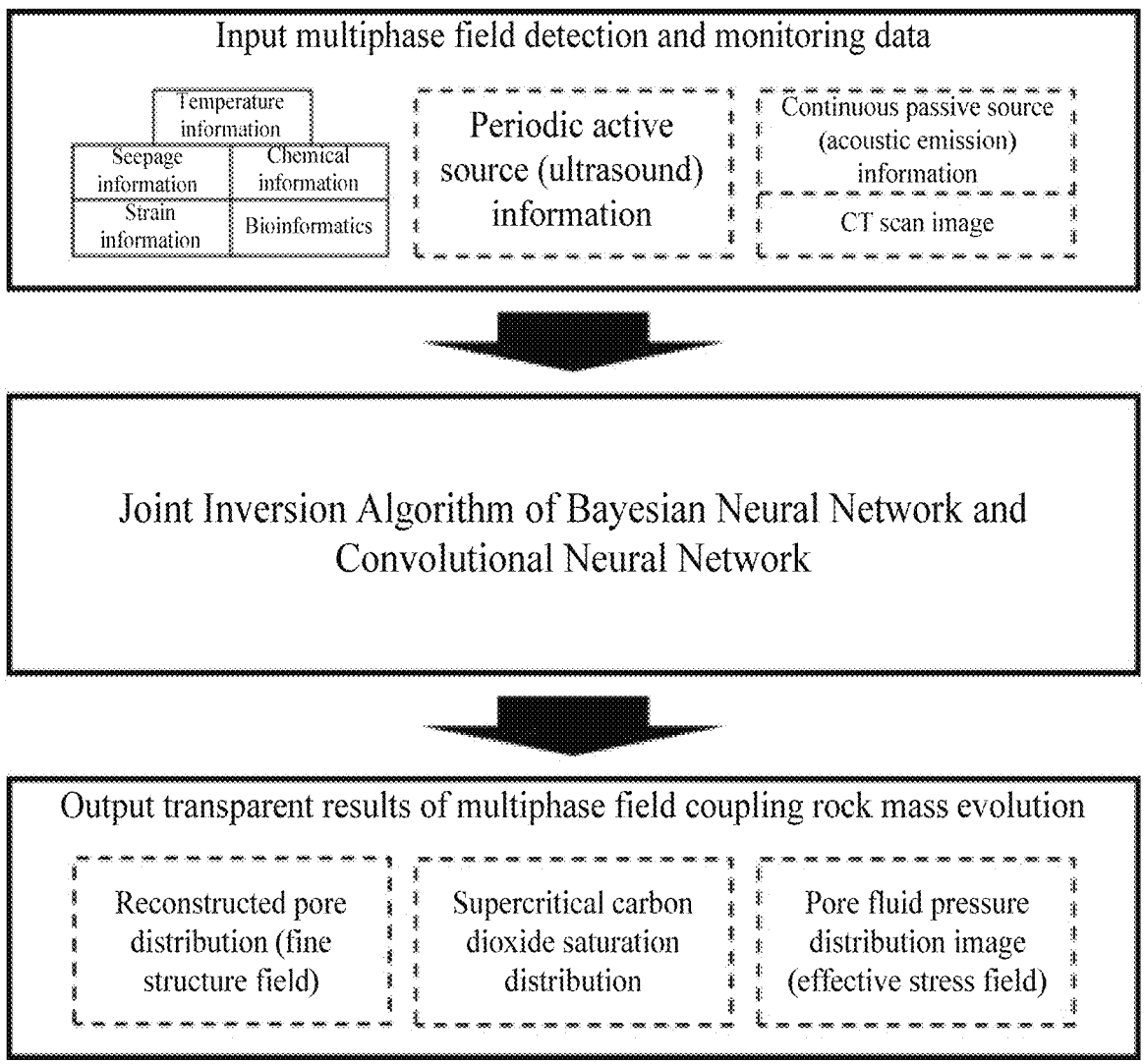
FIG. 4 a schematic diagram of the transparency characterization of multiphase field coupling rock mass evolution.

In an exemplary embodiment, as shown in FIG. 2 and FIG. 4, a real-time quantitative characterization method for rock mass evolution is provided, which is executed by a computer equipment. Specifically, it can be executed separately by a terminal or a server and the like, and can also be executed jointly by a terminal and a server. In this embodiment of the present application, the method is applied to the server 104 in FIG. 1 as an example for explanation, including the following S201 to S206.

S201, the evolution distribution images of the rock mass and the real-time multiphase field detection and monitoring data at different evolution stages in the whole testing process of the multiphase field coupling test are acquired, wherein the evolution distribution images include a reconstructed pore distribution image (fine structure field), a pore fluid pressure distribution image (effective stress field) and a supercritical carbon dioxide saturation distribution image; the multiphase field detection and monitoring data includes temperature, strain, resistivity, chemical ion concentration, microbial cell concentration, P wave velocity, S wave velocity and acoustic emission data, and are optical-electrical-acoustic signals.

S202, the real-time multiphase field detection and monitoring data is fused by utilizing the feature extraction method and the Transformer deep learning model; the feature extraction method includes but is not limited to a principal component analysis method.

Figure 3:
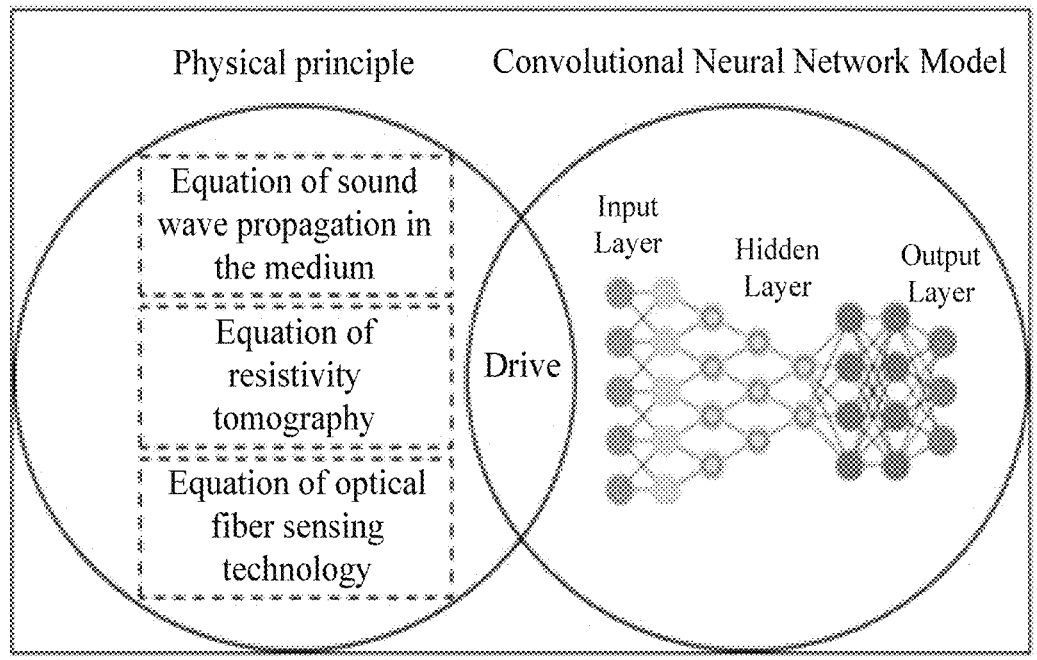
FIG. 3 a schematic diagram of a deep learning model driven by physical principles.

S203, a deep learning model driven by physical principles is established by utilizing the deep learning method according to the physical principles of fluid density under the influence of temperature, chemical ion concentration, microbial cell concentration and supercritical carbon dioxide, as shown in FIG. 3; the deep learning method includes: a Bayesian neural network, a convolutional neural network, a deep residual network, a recurrent neural network and a generative antagonistic network. Among them, the physical principles include: the equation of sound wave propagation in the medium, the equation of resistivity tomography and the equation of the optical fiber sensing technology.

S204, the deep learning model driven by physical principles is trained with the real-time fused data as input and the corresponding evolution distribution images as output.

S205, the evolution distribution images is obtained by adopting the trained deep learning model according to the multiphase field detection and monitoring data of different time and different types; the S205 realizes the real-time accurate imaging of the whole process of the deformation, damage and fracture evolution of the multi-phase field longtime coupling rock mass and the transparent characterization (transparent result) of the fine structure field, the effective stress field and the supercritical carbon dioxide migration in the rock mass.

S206, the quantitative characterization of the physical and mechanical parameters in the whole process of the progressive failure of the dynamic evolution of the rock mass is realized by adopting a mathematical model according to the macroscopic mechanical parameters and the evolution distribution images which are synchronous with the multiphase field detection and monitoring data; wherein the macroscopic mechanical parameters are the macroscopic mechanics parameters of different stages of rock mass evolution under the coupling action of different loading paths and multiphase fields, so that a multiphase field longtime coupling mechanism of reservoir rock matrix evolution and cover rock structure deterioration of the carbon sequestration engineering under a true three-dimensional stress state is revealed.

The mathematical model is established by logistic regression analysis, support vector machine (SVM), random forest or neural network.

S201-S206 proposed a real-time joint inversion method of multi-source heterogeneous data fusion and multiphase field parameters based on the big data analysis, the data mining and the machine learning, in order to achieve real-time and transparent characterization of multiphase field longtime coupling rock mass evolution.

The device for acquiring the real-time multiphase field detection and monitoring data includes but is not limited to the fiber optic sensors, the electrode sensor, and the ultrasonic transducers.

The evolution distribution images are determined as follows.

The different evolution stages of rock mass deformation, damage and crack initiation, cracking, expansion and penetration in the whole testing process of multiphase field coupling test are monitored in real time, and a large number of evolution distribution images before, during and after the test are obtained by CT technology scanning; the evolution distribution images are digital cores.

In order to realize the real-time and transparent characterization of the fine structure field, effective stress field and supercritical carbon dioxide migration in the rock mass under the multiphase field longtime coupling effect, a deep learning method driven by physical principles and a deep learning model with physical significance are established. Traditional methods of training deep learning models require a large amount of data, and the images of internal structure of rock mass and the images of fluid migration changes of rock mass and the corresponding multiphase field detection and monitoring data obtained by CT scanning test are limited, so it is difficult for the existing training methods to construct a high precision and universal deep learning model. Moreover, the established deep learning models often have only statistical significance and lack physical significance and interpretation. The deep learning model driven by physical principles is to be established by embedding controlling physical laws (i.e. partial differential equations) as prior information, combining differentiable programming methods with traditional numerical simulation methods (such as finite element method, finite difference method, or discrete element method), so that all numerical operations are implemented in differentiable building modules. The differentiable mechanism in this application solves forward and backward problems through automatic differentiation methods, and is relatively easy to combine with deep neural networks to build a universal deep learning model based on physical principles.

According to the present application, multi-source heterogeneous massive information is intelligently fused and cooperatively inverted, so that data and images of different formats, different magnitudes, different dimensions and different resolutions obtained by different detection and monitoring means are efficiently utilized; the key scientific problem of difficulty in training the deep learning model driven by physical principles is overcome to achieve the real-time transparent quantitative characterization of fine structural fields, effective stress fields, and supercritical carbon dioxide transport inside the multiphase field coupling rock mass.

Based on the same concept of the present disclosure, the embodiment of the present application further provides a real-time quantitative characterization equipment of rock mass evolution for implementing the above-mentioned real-time quantitative characterization method of rock mass evolution. The implementation solution for solving the problem provided by the equipment is similar to the implementation solution described in the above method, so the specific definition of one or more embodiments of the real-time quantitative characterization equipment for rock mass evolution provided below can refer to the definition of the above real-time quantitative characterization method for rock mass evolution, which is not described here.

In an exemplary embodiment, a real-time quantitative characterization equipment for rock mass evolution is provided, including:

the data acquisition module, which is configured to acquire the evolution distribution images of the rock mass and real-time multiphase field detection and monitoring data at different evolution stages in the whole testing process of the multiphase field coupling test, wherein the evolution distribution images include the reconstructed pore distribution image, the pore fluid pressure distribution image and the supercritical carbon dioxide saturation distribution image; the multiphase field detection and monitoring data includes temperature, strain, resistivity, chemical ion concentration, microbial cell concentration, P wave velocity, S wave velocity and acoustic emission data;

the data fusion module, which is configured to carry out data fusion for the real-time multiphase field detection and monitoring data by utilizing the feature extraction method and the Transformer deep learning model;

the deep learning model establishing module driven by physical principles, which is configured to establish a deep learning model driven by physical principles by utilizing the deep learning method according to the physical principles of the fluid density under the influence of the temperature, the chemical ion concentration, the microbial cell concentration and the supercritical carbon dioxide;

the deep learning model training module driven by physical principles, which is configured to train the deep learning model driven by physical principles with the real-time fused data as input and the corresponding evolution distribution images as output;

the evolution distribution images inversion module, which is configured to obtain the evolution distribution images by adopting the trained deep learning model according to the multiphase field detection and monitoring data of different time and different types; and the quantitative characterization module of physical and mechanical parameters, which is configured to realize the quantitative characterization of the physical and mechanical parameters in the whole process of the progressive failure of the dynamic evolution of the rock mass by adopting a mathematical model according to the macroscopic mechanical parameters and the evolution distribution images which are synchronous with the multiphase field detection and monitoring data.

In an exemplary embodiment, a computer equipment is provided, which may be a server or a terminal. The computer equipment includes a processor, a memory, an Input/Output (I/O) interface, and a communication interface. The processor, the memory and the I/O interface are connected through a system bus, and the communication interface is connected to the system bus through the I/O interface. Wherein the processor of the computer equipment is configured to provide computing and control capabilities. The memory of the computer equipment includes a non-volatile storage medium and an internal memory. The non-volatile storage medium stores an operating system, a computer program, and a database. The internal memory provides an environment for the operation of an operating system and a computer program in the non-volatile storage medium. An I/O interface of the computer equipment is used to exchange information between the processor and external equipment. The communication interface of the computer equipment is used for communicating with an external terminal through a network connection. This computer program is executed by a processor to implement a real-time quantitative characterization method for rock mass evolution.

In an exemplary embodiment, a computer equipment is provided, including a memory and a processor, wherein the memory stores a computer program, and the processor executes the steps of the above method embodiments if the computer program is executed.

In an exemplary embodiment, a computer-readable storage medium is provided, which stores a computer program, if executed by a processor, implements the steps of various method embodiments described above.

In an exemplary embodiment, a computer program product is provided, which includes a computer program, if executed by a processor, implements the steps of the various method embodiments described above.

It should be noted that the user information (including but not limited to user equipment information, user personal information, etc.) and data (including but not limited to data for analysis, stored data, displayed data, etc.) involved in the present application are information and data authorized by the user or fully authorized by all parties, and the collection, the use and the processing of relevant data need to comply with relevant regulations.

Those of ordinary skill in the art may understand that all or part of the processes for implementing the method of the above embodiments may be implemented by a computer program instructing relevant hardware, the computer program may be stored in a non-volatile computer-readable storage medium, and if being executed, the computer program may include the processes of the above embodiments. Wherein any reference to a memory, a database, or other medium used in the embodiments presented herein may include at least one of non-volatile and volatile memory. The non-volatile memory may include a Read-Only Memory (ROM), a magnetic tape, a floppy disk, a flash memory, an optical memory, a high-density embedded non-volatile memory, a Resistive Random Access Memory (ReRAM), a Magnetoresistive Random Access Memory (MRAM), a Ferroelectric Random Access Memory (FRAM), a Phase Change Memory (PCM), a graphene memory, and the like. The volatile memory may include a Random Access Memory (RAM), an external cache memory, or the like. By way of illustration and not limitation, RAM can be in a variety of forms, such as a Static Random Access Memory (SRAM) or a Dynamic Random Access Memory (DRAM), etc.

The databases involved in various embodiments provided herein may include at least one of a relational database and a non-relational database. The non-relational database may include, but is not limited to, a distributed database based on a blockchain. The processor involved in the embodiments provided in the present application may be a general-purpose processor, a central processing unit, a graphics processing unit, a digital signal processor, a programmable logic device, a data processing logic controller based on quantum computing, etc., and is not limited thereto.

The technical features of the above embodiments can be combined arbitrarily. For the sake of brevity, all possible combinations of the technical features of the above embodiments are not described. However, as long as there is no contradiction between the combinations of these technical features, they should be considered to be within the scope of the present specification. The principles and embodiments of the present application are described herein with specific examples, and the description of the above embodiments is only used to help understand the method and core idea of the present application; meanwhile, for those of ordinary skill in the art, there may be changes in the specific embodiments and application scope according to the idea of the application. In summary, the content of the present specification should not be construed as limiting the present application.

What is claimed is:

1. A real-time quantitative characterization method for rock mass evolution, comprising:
   acquiring evolution distribution images of the rock mass and real-time multiphase field detection and monitoring data at different evolution stages in a whole testing process of a multiphase field coupling test, wherein the evolution distribution images comprise a reconstructed pore distribution image, a pore fluid pressure distribution image and a supercritical carbon dioxide saturation distribution image; the real-time multiphase field detection and monitoring data comprises temperature, strain, resistivity, chemical ion concentration, microbial cell concentration, P wave velocity, S wave velocity and acoustic emission data;
   carrying out data fusion for the real-time multiphase field detection and monitoring data by utilizing a feature extraction method and a Transformer deep learning model;
   establishing a deep learning model driven by physical principles by utilizing a deep learning method according to physical principles of fluid density under the influence of temperature, chemical ion concentration, microbial cell concentration and supercritical carbon dioxide; the physical principles comprise: an equation of sound wave propagation in a medium, an equation of resistivity tomography and an equation of an optical fiber sensing technology;
   training the deep learning model driven by physical principles with the fused real-time multiphase field detection and monitoring data as input and the corresponding evolution distribution images as output;
   obtaining evolution distribution images by adopting the trained deep learning model according to the real-time multiphase field detection and monitoring data of different time and different types; and
   realizing quantitative characterization of physical and mechanical parameters in a whole process of progressive failure of dynamic evolution of the rock mass by adopting a mathematical model according to macroscopic mechanical parameters and the evolution distribution images which are synchronous with the real-time multiphase field detection and monitoring data; wherein the macroscopic mechanical parameters are macroscopic mechanics parameters of different stages of rock mass evolution undercoupling action of different loading paths and multiphase fields.

2. The real-time quantitative characterization method for rock mass evolution according to claim 1, wherein a device for acquiring the real-time multiphase field detection and monitoring data comprises an optical fiber sensor, an electrode sensor, and an ultrasonic transducer.

3. The real-time quantitative characterization method for rock mass evolution according to claim 1, wherein the deep learning method comprises a Bayesian neural network, a convolutional neural network, a deep residual network, a recurrent neural network and a generative adversarial network.

4. The real-time quantitative characterization method for rock mass evolution according to claim 1, wherein the mathematical model is established by logistic regression analysis, a support vector machine SVM, a random forest or a neural network.

5. A computer, comprising: a memory, a processor, and a computer program stored on the memory and executable by the processor, the processor executes the computer program to implement the real-time quantitative characterization method of rock mass evolution according to claim 1.

6. The computer according to claim 5, wherein a device for acquiring the real-time multiphase field detection and monitoring data comprises an optical fiber sensor, an electrode sensor, and an ultrasonic transducer.

7. The computer equipment according to claim 5, wherein the deep learning method comprises a Bayesian neural network, a convolutional neural network, a deep residual network, a recurrent neural network and a generative adversarial network.

8. The computer equipment according to claim 5, wherein the mathematical model is established by logistic regression analysis, a support vector machine SVM, a random forest or a neural network.

9. A real-time quantitative characterization device for rock mass evolution, comprising:
   a data acquisition module, which is configured to acquire evolution distribution images of the rock mass and real-time multiphase field detection and monitoring data at different evolution stages in a whole testing process of a multiphase field coupling test, wherein the evolution distribution images comprise a reconstructed pore distribution image, a pore fluid pressure distribution image and a supercritical carbon dioxide saturation distribution image; the real-time multiphase field detection and monitoring data comprises temperature, strain, resistivity, chemical ion concentration, microbial cell concentration, P wave velocity, S wave velocity and acoustic emission data;
   a data fusion module, which is configured to carry out data fusion for the real-time multiphase field detection and monitoring data by utilizing a feature extraction method and a Transformer deep learning model;
   a deep learning model establishing module driven by physical principles, which is configured to establish a deep learning model driven by physical principles by utilizing a deep learning method according to physical principles of fluid density under the influence of temperature, chemical ion concentration, microbial cell concentration and supercritical carbon dioxide;
   a deep learning model training module driven by physical principles, which is A configured to train the deep learning model driven by physical principles with the fused real-time multiphase field detection and monitoring data as input and the corresponding evolution distribution images as output; the physical principles comprise: an equation of sound wave propagation in a medium, an equation of resistivity tomography and an equation of an optical fiber sensing technology;

an evolution distribution images inversion module, which is configured to obtain evolution distribution images by adopting the trained deep learning model according to the real-time multiphase field detection and monitoring data of different time and different types; and a quantitative characterization module of physical and mechanical parameters, which is configured to realize quantitative characterization of physical and mechanical parameters in a whole process of progressive failure of dynamic evolution of the rock mass by adopting a mathematical model according to macroscopic mechanical parameters and the evolution distribution images which are synchronous with the real-time multiphase field detection and monitoring data; wherein the macroscopic mechanical parameters are macroscopic mechanics parameters of different stages of rock mass evolution undercoupling action of different loading paths and multiphase fields.

\* \* \* \* \*